United States Patent [19]

Hoeschele et al.

[11] Patent Number: 4,970,324
[45] Date of Patent: Nov. 13, 1990

[54] AMINOALKYL-SUBSTITUTED AZETIDINE PLATINUM(II) COMPLEXES

[76] Inventors: James D. Hoeschele, 3550 Terhune, Ann Arbor, Mich. 48104; David A. Berry, 756 Honey Creek Dr., Ann Arbor, Mich. 48103; Luigi G. Marzilli, 2221 Randolph Ct., Atlanta, Ga. 30345

[21] Appl. No.: 142,151

[22] Filed: Jan. 8, 1988

Related U.S. Application Data

[63] Continuation of Ser. No. 813,205, Dec. 24, 1985, abandoned.

[51] Int. Cl.$^5$ .................. A61K 31/555; C07F 16/00
[52] U.S. Cl. .................................. 548/950; 548/402; 548/955
[58] Field of Search .................. 548/402, 950, 955; 514/184

[56] References Cited

U.S. PATENT DOCUMENTS

| | | | |
|---|---|---|---|
| 4,410,544 | 10/1983 | Berg et al. | 514/492 |
| 4,584,316 | 4/1986 | Rosenberg et al. | 514/492 |
| 4,661,516 | 4/1987 | Brown et al. | 514/492 |
| 4,704,464 | 11/1987 | Brunner et al. | 548/402 X |
| 4,716,157 | 12/1987 | Bitha et al. | 514/184 |
| 4,822,892 | 4/1989 | Honda et al. | 548/402 |
| 4,902,797 | 2/1990 | Totani et al. | 546/11 |

FOREIGN PATENT DOCUMENTS 115929 8/1984 European Pat. Off.
176005 4/1986 European Pat. Off.

OTHER PUBLICATIONS

Sosnovsky, et al., Chemical Abstracts, vol. 101(17):143678s (10/22/84).
Connors, et al., Chemical Abstracts, vol. 78: 79753q (1973).
Simon, et al., Rev. Roum. Biochim., vol. 14(2), pp. 117-125 (1977).
Tobe, et al., Chemical Abstracts, vol. 80: 55897e (1974).
Douple, et al., Chemical Abstracts, vol. 89: 157244t (1978).
Honda, et al., Chemical Abstracts, vol. 105: 97698f(1986).
Honda, et al., Chemical Abstracts, vol. 108: 106470s, 106471t (1988).
Inagaki et al., Inorganica Chim. Acta, 37:L547-L548 (1979).
Proc. of the Am. Assoc. of Cancer Res., Abstr. 652, p. 166, Hacker, et al.
Tanabe Seiyaku KK, Derwent Abstract 85-272741/44 of Japan 184,015, 09/19/85.
Chugai Pharmaceutical KK, Derwent Abstract 85-240374/39 of Japan 158,195, 08/19/85.
Tanabe Seiyaku KK (II), Derwent Abstract 84-131256/21 of Japan 67,262, 04/16/84.
Simon, et al., Chemical Abstracts, vol. 87, 145547q (1977).
Bystrenina, et al., Chemical Abstracts, vol. 96, 85741x (1982).
Minacheva, et al., Chemical Abstracts, vol. 100, No. 25, 220572m (6/18/84).

*Primary Examiner*—Diana Rivers
*Attorney, Agent, or Firm*—Ruth H. Newtson

[57] ABSTRACT

Square-planar four-coordinate complexes of cis-platinum(II) with neutral bidentate aminoalkyl-substituted cycloalkylamine ligands and bromo-, chloro-, iodo-, nitrato-, oxalato-, or malanato-ligands possess antimicrobial activity as well as activity against transplanted L1210 and P388 murine leukemia cell lines.

2 Claims, No Drawings

AMINOALKYL-SUBSTITUTED AZETIDINE PLATINUM(II) COMPLEXES

This is a continuation application of U.S. Ser. No. 813,205 filed Dec. 24, 1985, now abandoned.

BACKGROUND OF THE INVENTION

The present invention is related to compounds having pharmacological activity, to pharmaceutical compositions containing these compounds, and to a pharmaceutical method. More particularly, this invention concerns square-planar cis-platinum (II) four-coordinate complexes having anti-microbial activity as well as activity against the L1210 and P388 murine leukemia cell lines, to pharmaceutical compositions containing these complexes, and to methods of treating microbial infections and of inhibiting the growth of neoplasms in a mammal.

SUMMARY AND DETAILED DESCRIPTION

In its broadest aspect, the present invention provides square-planar cis-platinum(II) four-coordinate complexes having the formula

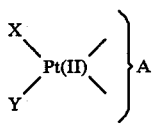

where A is a neutral bidentate aminoalkylcyclo(aza)alkane ligand selected from

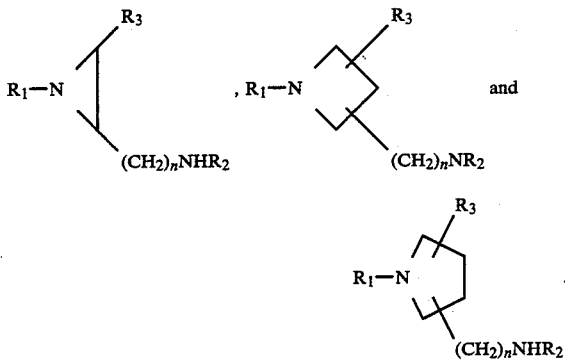

The integer n may take on a value of from one to three, and $R_1$ and $R_2$ are independently hydrogen, straight or branched alkyl of from one to four carbon atoms, straight or branched alkyl of from one to four carbon atoms substituted with hydroxy or alkoxy of from one to four carbon atoms, cycloalkyl of from three to six carbon atoms, or benzyl.

$R_3$ is hydrogen, hydroxy, carboxyl, straight or branched alkyl of from one to four carbon atoms, straight or branched hydroxyalkyl of from one to four carbon atoms, straight or branched alkyl of from one to four carbon atoms substituted with alkoxy of from one to four carbon atoms, cycloalkyl of from three to six carbon atoms, or benzyl.

X and Y are negatively-charged monodentate ligands which may be the same or different and are selected from chloro, bromo, iodo, nitrato; or where X and Y taken together form a dinegatively-charged bidentate ligand selected from sulfato, oxalato, and

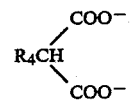

where $R_4$ is hydrogen, hydroxy, amino, alkyl of from one to four carbon atoms, benzyl, hydroxyalkyl of from one to four carbon atoms, or aminoalkyl of from one to four carbon atoms.

In the complexes of this invention, the ligand A is complexed to the central platinum atom through the nitrogen atom of the cyclo(aza)alkane ring and the nitrogen atom of the aminoalkyl substituent of the ligand group A.

In solution, either of the X and Y ligands of the complexes of this invention may be replaced by solvent.

Specific examples of compounds falling within the scope of this invention iclude the following:

(SP-4-3)-(2-aziridinemethanamine-$N^1,N^2$)dichloro)-platinum.

(SP-4-3)-(2-aziridinemethanamine-$N^1,N^2$)[propanedioato(2-)-O,O']platinum.

(SP-4-3)-dichloro(1-ethyl-2-aziridinemethanamine-$N^1,N^2$)platinum.

(SP-4-3)-(1-ethyl-2-aziridinemethanamine-$N^{\alpha},N^1$)[propanedioato (2-)-O,O']platinum.

(SP-4-3)-dichloro(2-azetidinemethanamine-$N^1,N^2$)-platinum.

(SP-4-3)-dichloro(3-methyl-3-azetidinemethanamine-$N^1,N^3$)platinum.

(SP-4-3)-(1-ethyl-2-azetidinylmethanamine-$N^1,N^2$)-propanedioato(2-)-O,O']platinum.

[SP-4-3-]-dichloro(2-pyrrolidinemethanamine-$N^1,N^2$)-platinum.

(SP-4-3)-(2-pyrrolidinemethanamine, $N^1,N^2$)[propanedioato-(2-)-O,O']platinum.

(SP-4-3)-dichloro(1-methyl-2-pyrrolidineethanamine-$N^1,N^2$)platinum.

(SP-4-3)-dichloro(1-ethyl-2-pyrrolidinemethanamine-$N^1,N^2$)platinum.

(SP-4-3)-(1-ethyl-2-pyrrolidinemethanamine-$N^1,N^2$)[propanedioato(2-)-O,O']platinium.

(SP-4-3)-dichloro(3-pyrrolidinemethanamine-$N^1,N^3$)platinum.

(SP-4-3)-dichloro(1-ethyl-3-pyrrolidinemethanamine-$N^1,N^3$)platinum.

The platinum complexes of this invention may include one or more chiral centers and may thus exist in several different isomeric forms. The present invention contemplates all possible isomeric forms of the claimed platinum complexes.

The platinum complexes of the present invention are prepared by the following general methods.

Potassium iodide, either as a solid or as a previously prepared solution in water, is added to an aqueous solution of potassium tetrachloroplatinate. Sufficient potassium iodide is employed to give a molar ratio of iodine to platinum of about 6 to 1. This mixture is stirred at ambient temperature for a sufficient time, usually about 15–30 minutes, to allow complete conversion of the red tetrachloroplatinate solution to the dark-colored solution of $K_2PtI_4$.

To this solution is added the desired diamine, A, causing the precipitation of the complex $PtAI_2$. The color of this complex generally ranges from dark brown to green to yellow. After allowing this reaction to proceed at ambient temperature for a period of about 30 minutes, the mixture is warmed to about 40°–45° C. for five minutes, and then stirred for an addition two hours at ambient temperature. The precipitate is collected by filtration, washed with water, aqueous ethanol, absolute ethanol, and finally diethyl ether and dried to yield the complex where X and Y are iodide.

If it is desired that the ligands X and Y are nitrato, the complex $PtAI_2$ is treated with aqueous silver nitrate to precipitate silver iodide. The mixture is filtered, and the filtrate is evaporated to dryness to yield the $PtA(NO_3)_2$ complex. The sulfato complex, $PtASO_4$ is likewise produced by precipitation of silver iodide from the $PtAI_2$ complex by means of silver sulfate.

The dichloro- and dibromo- complexes, where X and Y are both chloride or bromide, are produced from the $PtAI_2$ complex by first precipitating silver iodide by the addition of silver nitrate and filtration, followed by treatment of the filtrate with dilute aqueous hydrochloric or hydrobromic acid, respectively.

For example, to prepare the complex $PtACl_2$, a solution containing about a 2% stoichiometric excess of silver nitrate is added to the $PtAI_2$ complex, stirred at ambient temperature for about 30 minutes, warmed to 40°–45° C. for five minutes, and then stirred at ambient temperature for an additional 1–2 hours. The precipitated silver iodide is removed by filtration, and the filtrate treated with a stoichiometric excess of hydrochloric acid. The resulting solution is partially evaporated under vacuum and cooled to induce the precipitation of the $PtACl_2$ complex which is collected by filtration. This product is washed successively with cold dilute hydrochloric acid, ethanol, and diethyl ether and dried.

To form the oxalato- or malanoto-complexes, the $PtAI_2$ complex is treated with silver sulfate solution to precipitate silver iodide, filtered, and the resulting filtrate treated with barium hydroxide to remove the sulfate. This mixture is filtered, and the filtrate is reacted with a a stoichiometrically equivalent amount of oxalic or malonic acid to form the appropriate complexes. The resulting solutions are concentrated, and the precipitated complexes are collected by filtration, washed and dried.

The platinum complexes of the present invention possess antimicrobial activity against DNA repair deficient strains of *Saccharomyces cerevisiae* and *Schizosaccharomyces pombe* (technique detailed in Nestmann et al., *Can. J. Genet. Cytol.*, 24: 771–775 (1982)) and *E. coli*, (technique detailed in Quillardet et al., *Proc. Natl. Acad. Sci.* (USA), 79: 5971–5975 (1982) and Tweats et al., *Carcinogenesis* (London), 2: 189–194 (1981)).

Moreover, the complexes of the present invention demonstrate activity against the L1210 and P388 murine leukemia cell lines. The screening tests employing these cell lines are described in Geran et al., "Protocols for Screening Chemical Agents and Natural Products Against Animal Tumors and Other Biological Systems," *Cancer Chemotherapy Reports*, Part 3, Vol. 3, No. 2, pp. 1–85 (1972). The L1210 and P388 screening methods have been cited as the best tools for predicting clinical utility of drugs in the treatment of human solid tumors as well as human leukemias and lymphomas (Venditti, "Relevance of Transplantable Animal Tumor Systems to the Selection of New Agents for Clinical Trial," Pharmacological Basis of Cancer Chemotherapy, Williams & Williams Pub. Co., (1975).

In Table 1, the ratio of median survival time of laboratory mice which had been treated with the test compound to untreated control animals is expressed as a percentage (% T/C values). Laboratory mice were implanted intraperitoneally with the L1210 murine leukemia cell line on day 0 and treated with intraperitoneal injections of representative platinum complexes of the present invention on days 3 and 7 at the dosages indicated. Data for the prior art complex cis-diamminedichloroplatinum(II) (cisplatin) is included for comparison.

TABLE 1

$$A \begin{Bmatrix} \diagdown \\ \diagup \end{Bmatrix} Pt \begin{matrix} \diagup Y \\ \diagdown X \end{matrix}$$

| A | X | Y | Dose (mg/kg) | % T/C* |
|---|---|---|---|---|
| 2-Aziridinemethanamine | Cl | Cl | 100 | 138 |
| 2-Aziridinemethanamine | Malanato | | 95 | 132 |
| 1-Ethyl-2-aziridine-methanamine | Cl | Cl | 20 | 152 |
| | | | 40 | 202 |
| | | | 50 | 173 |
| 1-Ethyl-2-aziridine-methanamine | Melanato | | 400 | 152 |
| 3-Methyl-3-azetidine-methanamine | Cl | Cl | 12.5 | 175 |
| 1-Ethyl-2-azetidine-methanamine | Cl | Cl | 40 | 162 |
| | | | 50 | 150 |
| 2-Pyrrolidineme-methanamine | Cl | Cl | 12.5 | 186 |
| 2-Pyrrolidine-methanamine | Malanato | | 25 | 162 |
| 3-Pyrrolidine-methanamine | Cl | Cl | 20 | 200 |
| 1-Methyl-2-pyrrol-idineethanamine | Cl | Cl | 50 | 169 |
| | | | 69 | 184 |
| 1-Ethyl-2-pyrrol-idinemethanamine | Cl | Cl | 50 | 172 |
| | | | 80 | 168 |
| $(NH_3)_2$ (Cisplatin prior art) | Cl | Cl | 8 | 288 |

*% T/C values are the ratios of median survival times in days) of treated to control mice.

In Table 2, the efficacy of platinum complexes of the present invention is shown as measured against strains of L1210 and P388 cell lines which were selected for their resistance to cis-diamminedichloroplatinum(II) (cisplatin). $ID_{50}$ values were determined for each compound shown in the Table as measured against the normal L1210 and P388 cell lines as well as against L1210 and P388 cell lines which were selected for their resistance to cisplatin at a concentration of 4 $\mu g/ml$. $ID_{50}$ values are the concentration of complex required to inhibit the in vitro growth of treated cells to a level of 50% of that for untreated cells over a 72 hour period. The cell lines are suspended in appropriate media at a concentration which results in the cells remaining in log phase growth throughout the treatment period. Serially diluted drug is added to duplicate wells containing the cell growth. After 72 hours of incubation of the cell lines in 5% $CO_2$, the cells are counted and the $ID_{50}$ values determined.

Resistance ratio values shown in Table 2 were calculated by dividing the $ID_{50}$ values against the resistant cell lines by the $ID_{50}$ values against the normal cell lines. The resistance ratio values shown in the Table indicate a measure of the degree of resistance of the cell line to a particular drug. Thus, the higher the resistance ratio, the less effective is the drug against the cisplatin resitant cell line.

TABLE 2

$$A\begin{Bmatrix} \diagdown & \diagup Y \\ & Pt \\ \diagup & \diagdown X \end{Bmatrix}$$

| A | X | Y | Resistance Ratios L1210 | Resistance Ratios P388 |
|---|---|---|---|---|
| 1-Ethyl-2-aziridine-methanamine | Cl | Cl | 12.6 | 1.96 |
| 3-Methyl-3-azetidine-methanamine | Cl | Cl | 0.89 | >13.1 |
| 2-Pyrrolidinemethane-amine | Cl | Cl | 3.88 | 1.5 |
| 2-Pyrrolidinemethan-amine | Malanato | | 5.9 | — |
| 3-Pyrrolidinemethan-amine | Cl | Cl | 8.86 | — |
| 1-Methyl-2-pyrrolidineethanamine | Cl | Cl | 1.25 | — |
| 1-Ethyl-2-pyrrolidinemethanamine | Cl | Cl | 4.58 | — |
| $(NH_3)_2$ (Cisplatin prior art) | Cl | Cl | 7.93 | 15.9 |

The data in Tables 1 and 2 indicate that, while the complexes of the present invention are less potent than cis-platin, they are more effective against the L1210 and P388 platinum-resistant cell lines.

For preparing pharmaceutical compositions from the compounds of this invention, inert, pharmaceutically acceptable carriers can be either solid or liquid. Solid form preparations include powders, tablets, dispersable granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions or sterile physiological saline solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation in is unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

In therapeutic use as antineoplastic agents, the compounds utilized in the pharmaceutical method of this invention are administered to the patient preferably in daily intravenous doses of from 50 to 120 mg/m$^2$ of body area on a regimen of from one to seven days, repeated as needed after a hiatus of from two to six weeks.

The specific dosages and dosage regimen employed, however, may be varied depending upon the requirements of the patient, the severity of the condition being treated, and the activity of the compound being employed. The determination of optimum dosages for a particular situation is within the skill of the art.

The following preparative examples are provided to enable one skilled in the art to practice the invention, and are illustrative thereof. They are not to be read as limiting the scope of the invention as it is defined by the appended claims.

EXAMPLE 1

Preparation of (SP-4-3)-Dichloro(1-ethyl-2-azetidinemethanamine-N$^1$,N$^2$)platinum Potassium iodide (9.96 g, 60 mmol) was added to an aqueous solution of potassium tetrachloroplatinate (4.15 g, 10 mmol) and the resulting solution was stirred at ambient temperature for 15 minutes. During this time, the K$_2$PtCl$_4$ solution was converted into a dark solution of K$_2$PtI$_4$. To this solution was added 1-ethyl-2-azetidinemethanamine (1.23 g, 10.8 mmol, previously prepared from methyl 2,4-dibromobutyrate by the method of Cromwell, *J. Het. Chem.*, 5: 309 (1968)) in one portion with vigorous stirring, resulting in the formation of a yellow-green precipitate. After sitrring at ambient temperature for 30 minutes, the mixture was warmed to 40° C. for five minutes, and then stirred at ambient temperature for an additional two hours.

The precipitated solid was collected by filtration, washed with cold water, 50% aqueous ethanol, a small amount of 95% ethanol, and finally with diethyl ether. This material was air-dried for 30 minutes to give 5.46 g (97%) of cis-PtAI$_2$ where A represents 1-ethyl-2-azetidinemethanamine.

To a stirred slurry of cis-PtAI$_2$ in 40 ml of water was added a solution of 3.38 g (19.88 mmol) of silver nitrate in 20 ml of water. The mixture was stirred for 30 minutes, warmed to 40° C. for five minutes, and then stirred at ambient temperature for 1.5 hours. After this time, the mixture was cooled to about 10° C., and filtered to remove the precipitated silver iodide. Hydrochloric acid (1.94 mmol) was added to the filtrate.

The acidified filtrate was warmed to 40° C. briefly, cooled, and the precipitated solid collected by filtration. The filtrate was checked for the presence of silver ion by the addition of a small amount of aqueous HCl. No further precipitate was evident.

To the filtrate was added 42.5 ml of 0.911 M HCl (38.8 mmol) and the solution was warmed for five minutes. The light-yellow aqueous solution was concentrated to about 20 ml under vacuum, cooled, and the yellow solid which precipitated was collected by filtration. This material was washed with cold ethanol and diethyl ether and dried under vacuum at 40° C. for two hours to yield 2.99 g (79%) of (SP-4-3)-dichloro-(1-ethyl-2-azetidinemethanamine-N$^1$,N$^2$)platinum.

| Analysis - For C$_6$H$_{14}$N$_2$Cl$_2$Pt (Mol. wt. 380.19) | |
|---|---|
| Calc.: | C, 18.95%; H, 3.71%; N, 7.37%; Cl, 18.65% |
| Found: | C, 19.07%; H, 3.64%; N, 7.46%; Cl, 18.68%. |

The infrared spectrum (Nujol mull) of the product showed principal absorption peaks at 622, 654, 772, 957, 1002, 1090, 1145, 1178, 1246, 1380, 1457, 1592, 3127, 3191, and 3304 reciprocal centimeters.

The $^{13}$C nuclear magnetic resonance spectrum (DMF) of the product showed signals at 12.48, 18.66, 52.9, 58.35, 60.74, and 76.53 parts per million downfield from tetramethylsilane.

EXAMPLE 2

Preparation of
[SP-4-3-(S)]-Dichloro-(2-pyrrolidinemethanamine-N$^1$,N$^2$)platinum An aqueous solution of potassium tetrachloroplatinate (4.15 g, 10 mmol) was converted to a solution of potassium tetraiodoplatinate by reaction with 9.96 g (6 mmol) of potassium iodide after the manner of Example 1.

To this solution was added 2-pyrrolidinemethanamine (1.0 g, 10 mmol, previously prepared by the LiAlH$_4$ reduction of 1-prolinamide after the method of von S. Schnell, *Helv. Chim. Acta*, 38: 2036 (1955)) in one portion with vigorous stirring. Reaction and work-up of this mixture after the manner of Example 1 yielded 5.32 g (97% of cis-PtAI$_2$ where A represents 2-pyrrolidinemethanamine.

Treatment of this material with hydrochloric acid, and work-up after the manner of Example 1, produced 3.04 g (83%) of [SP-4-3]-dichloro(2-pyrrolidinemethanamine-N$^1$,N$^2$)-platinum.

| Analysis - For C$_5$H$_{12}$N$_2$Cl$_2$Pt (Mol. wt. 367.07) | |
|---|---|
| Calc.: | C, 16.36%; H, 3.29%; N, 7.63%; Cl, 19.32% |
| Found: | C, 16.50%; H, 3.32%; N, 7.64%; Cl, 19.05%. |

The infrared spectrum (Nujol mull) of the product showed principal absorption peaks at 724, 785, 936, 982, 1025, 1084, 1149, 1187, 1378, 1584, 3001, and 3233 reciprocal centimeters.

The $^{13}$C nuclear magnetic resonance spectrum (DMF) of the product showed signals at 25.25, 61.6, 52.14 and 67.35 parts per million downfield from tetramethylsilane.

EXAMPLE 3

Preparation of
(SP-4-3)-Dichloro(1-ethyl-2-aziridinemethanamine-N$^1$,N$^2$)platinum Employing the general method of Example 1, 9.96 g (60 mmol) of potassium iodide and 4.15 g (10 mmol) of potassium tetrachloroplatinate were converted to a solution of potassium tetraiodoplatinate, which was then reacted with 1.03 g (10.3 mmol) of 1-ethyl-2-aziridinemethanamine to produce 5.28 g (96%) of cis-PtAI$_2$ where A represents 1-ethyl-2-aziridinemethanamine.

Employing the method of Example 1, this material was converted by the action of hydrochloric acid to 3.0 g (82%) of (SP-4-3)-dichloro(1-ethyl-2-aziridinemethanamine-N$^1$,N$^2$)-platinum.

| Analysis - For C$_5$H$_{12}$N$_2$Cl$_2$Pt (Mol. wt. 366.7) | |
|---|---|
| Calc.: | C, 16.40%; H, 3.30%; N, 7.65%; Cl, 19.36% |
| Found: | C, 16.57%; H, 3.19%; N, 7.75%; Cl, 19.35%. |

The infrared spectrum (Nujol mull) of the product showed principal absorption peaks at 787, 941, 956, 1037, 1069, 1176, 1209, 1224, 1386, 1399, 1456, 1467, 1591, 3130, 3188, and 3250 reciprocal centimeters.

The $^{13}$C nuclear magnetic resonance spectrum (DMF) of the product showed signals at 13.6, 41.5, 48.7, and 55.4 parts per million downfield from tetramethylsilane.

EXAMPLE 4

Preparation of
(SP-4-3)-Dichloro-(2-aziridinemethanamine-N$^1$,N$^2$)platinum

Employing the method of Example 1, 19.92 g (120 mmol) of potassium iodide and 8.3 g (20 mmol) of potassium tetrachloroplatinate were converted to an aqueous solution of potassium tetraiodoplatinate. This solution was reacted with 1.45 g (20 mmol) of 2-aziridinemethanamine to yield, after work-up in the manner described in Example 1, 9.57 g (92%) of cis-PtAI$_2$ where A represents 2-aziridinemethanamine.

This material was converted by hydrochloric acid, after the manner of Example 1, to yield a first crop of crystals weighing 1.37 g and, after further concentration of the mother liquor, a second crop of crystals weighing 2.73 g for a total of 4.10 g (63%) of (SP-4-3)-dichloro(2-aziridinemethanamine-N$^1$,N$^2$)platinum.

| Analysis - For $C_3H_8N_2Cl_2Pt$ (Mol. wt. 388.11) | |
|---|---|
| Calc.: | C, 10.65%; H, 2.38%; N, 8.29%; Cl, 20.97% |
| Found: | C, 10.87%; H, 2.32%; N, 8.29%; Cl, 20.86%. |

The infrared spectrum (Nujol mull) of the product showed principal absorption peaks at 632, 757, 833, 889, 925, 980, 1002, 1107, 1138, 1167, 1194, 1231, 1304, 1378, and 1463 reciprocal centimeters.

The $^{13}C$ nuclear magnetic resonance spectrum (DMF) of the product showed signals at 39.9, 49.1 and 30.61 parts per million downfield from tetramethylsilane.

EXAMPLE 5

Preparation of
(SP-4-3)-1-Ethyl-2-azetidinemethanamine-$N^1,N^2$)[propanediaoato(2-)-O,O']platinum Potassium iodide (9.96 g, 60 mmol) was added to an aqueous solution of 4.15 g (10 mmol) of potassium tetrachloroplatinate and the mixture was stirred at room temperature for 15 minutes during which a dark solution of $K_2PtI_4$ formed.

To this solution was added, in one portion with vigorous stirring, 1.2 g (10.5 mmol) of 1-ethyl-2-azetidinemethanamine which had been previously prepared from methyl 2,4-dibromobutyrate by the method of Cromwell, J. Het. Chem., 5: 309 (1968).

After stirring this mixture at room temperature for 30 minutes, it was warmed to 40° C. for five minutes and then allowed to stir at ambient temperature overnight while being protected from light. The yellow solid which formed was collected by filtration, washed successively with water, 50% aqueous ethanol, and finally with cold 95% ethanol. The solid was air dried to yield 5.4 g (96%) of cis-PtAI$_2$ where A represents 1-ethyl-2-azetidinemethanamine.

The cis-PtAI$_2$ was added in one portion to a solution of 2.99 g (9.6 mmol) of silver sulfate in warm (45° C.) water. This mixture was stirred overnight and then filtered to remove the precipitate silver iodide. The filtrate was concentrated under vacuum to a final volume of 50 ml, and 0.99 g (9.6 mmol) of malonic acid and 49 ml of 0.196 M barium hydroxide solution were added. This mixture was stirred overnight while being protected from light. The precipitated barium sulfate was removed by filtration, and the filtrate was lyophilized. The residue was dissolved in methanol and, upon standing, the desired product crystallized from the solution. The product was collected by filtration and dried to give 2.7 g (66%) of (SP-4-3)-1-ethyl-2-azetidinemethanamine-$N^1,N^2$)[propanediaoato-(2-)-O,O']platinum.

| Analysis - For $C_9H_{16}N_2O_4Pt$ | |
|---|---|
| Calc.: | C, 26.28%; H, 3.92%; N, 6.81% |
| Found: | C, 26.45%; H, 3.83%; N, 6.66%. |

The infrared spectrum (Nujol mull) of the product showed principal absorption peaks at 594, 648, 743, 958, 971, 1006, 1380, 1460, 1639, 1649, 3108, and 3205 reciprocal centimeters.

The $^{13}C$ nuclear magnetic resonance spectrum (D$_2$O) of the product showed signals at 14.65, 20.90, 49.92, 50.19, 50.45, 53.76, 60.83, 60.93, 63.59, 77.75, 180.76, and 180.95 parts per million downfield from tetramethylsilane.

EXAMPLE 6

Preparation of
(SP-4-3)-2-Aziridinemethanamine-$N^1,N^2$)-[propanedioato-(2-)-O,O']platinum In the manner of Example 5, 9.96 g (60 mmol) of potassium iodide and 4.15 g (10 mmol) of potassium tetrachloroplatinate were converted to an aqueous solution of potassium tetraiodoplatinate. This solution was reacted with 2-aziridinemethanamine (previously prepared by the method of Piper, J. Med. Chem., 22: 634 (1979)) to produce 4.82 g (93%) of cis-PtAI$_2$ where A represents 2-aziridinemethanamine.

This material was converted, by treatment with silver sulfate and 1.04 g (10 mmol) of malonic acid in the presence of barium hydroxide in the manner of Example 5, to 2.13 g (58.5%) of (SP-4-3)-2-aziridinemethanamine-$N^1,N^2$)[propanedioato-(2-)-O,O']platinum. This material was further purified by chromatography over silica gel, eluting with methanol.

| Analysis - For $C_6H_{10}N_2O_4Pt$ (Mol. wt. 369.25) | |
|---|---|
| Calc.: | C, 19.51%; H, 2.73%; N, 7.58% |
| Found: | C, 19.70%; H, 2.77%; N, 7.42%. |

The infrared spectrum (Nujol mull) of the product showed principal absorption peaks at 591,667, 748, 791, 848, 903, 933, 962, 996, 1029, 1076, 1104, 1151, 1192, 1234, 1387, 1459, 1598, 1629, 3163 reciprocal centimeters.

The $^{13}C$ nuclear magnetic resonance spectrum (D$_2$O) of the product showed signals at 20.31, 34.33, 41.32, 50.00, 50.33, 163.5, 180.92 parts per million downfield from tetramethylsilane.

EXAMPLE 7

Preparation of
(SP-4-3)-1-Ethyl-2-aziridinemethanamine-$N^1,N^2$)[propanedioato(2-)-O,O']platinum Employing the method of Example 5, potassium iodide (9.96 g (60 mmol) and potassium tetrachloroplatinate were reacted to produce an aqueous solution of potassium tetraiodoplatinate. This material was reacted with 1.15 g (10 mmol) of 1-ethyl-2-aziridinemethanamine to produce 5.34 g (97%) of cis-PtAI$_2$ where A represents 1-ethyl-2-aziridinemethanamine.

This material was converted by reaction with silver sulfate and then with malonic acid in the presence of barium hydroxide in the manner of Example 5, to 2.12 g (53%) of (SP-4-3)-1-ethyl-2-aziridinemethanamine-$N^1,N^2$)[propanedioato(2-)-O,O']platinum.

| Analysis - For $C_8H_{14}N_2O_4Pt$ (Mol. wt. 397.3) | |
|---|---|
| Calc.: | C, 24.18%; H, 3.55%; N, 7.05% |
| Found: | C, 24.46%; H, 3.48%; N, 6.86%. |

The infrared spectrum (Nujol mull) of the product showed principal absorption peaks at 598, 763, 791, 848, 877, 937, 973, 1033, 1078, 1138, 1226, 1254, 1320, 1386, 1411, 1640, and 2994 reciprocal centimeters.

The $^{13}C$ nuclear magnetic resonance spectrum (D$_2$O) of the product showed signals at 15.53, 44.16, 49.82, 50.23, 50.40, 57.89, 180.81, 180.87 parts per million downfield from tetramethylsilane.

EXAMPLE 8

Preparation of (SP-4-3)-(2-Pyrrolidinemethanamine-$N^1$, $N^2$)[propanedioato(2-)-O,O']platinum In the manner of Example 5, 9.96 g (60 mmol) of potassium iodide and 4.16 g (10 mmol) of potassium tetrachloroplatinate were reacted to form an aqueous solution of potassium tetraiodoplatinate. This material was reacted with 1.15 g of 2-pyrrolidinemethanamine (previously prepared by the LiAlH$_4$ reduction of 1-prolinamide after the method of vn S. Schnell, *Helv. Chim. Acta.*, 38: 2036 (1955)) to form 5.33 g (97%) of cis-PtAI$_2$ where A represents 2-pyrrolidinemethanamine.

This material was converted, after the manner of Example 5 to 1.9 g (48%) of (SP-4-3)-(2-pyrrolidinemethanamine-$N^1$,$N^2$)[propanedioato(2-)-O,O']platinum.

| Analysis - For C$_8$H$_{14}$N$_2$O$_4$Pt (Mol. wt. 397.3) | |
|---|---|
| Calc.: | C, 24.18%; H, 3.55%; N, 7.05% |
| Found: | C, 24.35%; H, 3.58%; N, 7.28%. |

The infrared spectrum (Nujol mull) of the product showed principal absorption peaks at 509, 558, 743, 807, 919, 966, 998, 1034, 1052, 1082, 1153, 1223, 1270, 1366, 1461, 1608, 1568, and 3220 reciprocal centimeters.

The $^{13}$C nuclear magnetic resonance spectrum (D$_2$O) of the product showed signals at 27.0, 49.95, 50.07, 50.22, 50.46, 53.01, 53.98, 68.91 and 180.98 parts per million downfield from tetramethylsilane.

EXAMPLE 9

Preparation of (SP-4-3)-1-Ethyl-2-pyrrolidinemethanamine-$N^1$,$N^2$)[propanedioato(2-)O,O']platinum Employing the method of Example 5, 9.96 g (60 mmol) of potassium iodide and 4.15 g (10 mmol) of potassium tetrachloroplatinate were reacted to form an aqueous solution of potassium tetraiodoplatinate. This material was reacted with 1.28 g (10 mmol) of 1-ethyl-2-pyrrolidinemethanamine (Aldrich Chemical Company, Milwaukee, Wis., USA) to produce 5.6 g (97%) of cis-PtAI$_2$ where A represents 1-ethyl-2-pyrrolidinemethanamine.

This material was further converted, after the method of Example 5, to produce 2.3 g of (SP-4-3)-1-ethyl-2-pyrrolidinemethanamine-$N^1$,$N^2$)[propanedioato(2-)O,O']platinum.

| Analysis - For C$_{10}$H$_{18}$N$_2$O$_4$Pt.1.6 H$_2$O | |
|---|---|
| Calc.: | C, 26.41%; H, 4.71%; N, 6.16% |
| Found: | C, 26.55%; H, 4.68%; N, 5.99%. |

The infrared spectrum (Nujol mull) of the product showed principal absorption peaks at 743, 836, 937, 1000, 1046, 1074, 1118, 1378, 1465, 1637, and 3001 reciprocal centimeters.

The $^{13}$C nuclear magnetic resonance spectrum (D$_2$O) of the product showed signals at 12.6, 22.25, 25.84, 47.1, 48.9, 57.3, 59.5, 75.08, 76.0, 173.54, and 177,85 parts per million downfield from tetramethylsilane.

EXAMPLE 10

Preparation of (SP-4-3)-3-Pyrrolidinemethanamine-$N^1$, $N^2$)[propanedioato(2-)-O,O']platinum After the manner of Example 5, 13.62 g (82 mmol) of potassium iodide and 5.68 g (13.7 mmol) of potassium tetrachloroplatinate were reacted to produce an aqueous solution of potassium tetraiodoplatinate. This solution was reacted with 3-pyrrolidinemethanamine (Scarborough et al., *J. Org. Chem.*, 26: 4955 (1961)) to produce 7.4 g (98%) of cis-PtAI$_2$ where A represents 3-pyrrolidinemethanamine.

This complex was added with vigorous stirring in one portion to a solution of 4.25 g (13.62 mmol) of silver sulfate at 45° C. This mixture was stirred at ambient temperature overnight while being protected from light, and then filtered to remove the precipitated silver iodide.

The filtrate was concentrated under vacuum to a volume of 50 ml, whereupon 1.42 g (13.62 mmol) of malonic acid and 69.5 ml of 0.196 M Ba(OH)$_2$ solution were added. This mixture was stirred at ambient temperature overnight. The precipitated barium sulfate was removed by filtration and the filtrate was lyophilized. The residue was dissolved in 150 ml of hot methanol and concentrated to a final volume of about 30 ml over a steam bath. Upon cooling, a white solid precipitated which was washed with diethyl ether and dried under vacuum to give 2.1 g (39%) of (SP-4-3)-3-pyrrolidinemethanamine-$N^1$,$N^2$)[propanedioato(2-)-O,O']platinum.

EXAMPLE 11

Preparation of (SP-4-3)-dichloro(1-ethyl-3-pyrrolidinemethanamine-$N^1$,$N^3$)platinum Employing 6.84 g of potassium tetrachloroplatinate, 16.4 g of potassium iodide and 2.00 g of 1-ethyl-3-aminomethylpryyolidine (Scarborough et al., *J. Org. Chem.*, 26: 4955 (1961)), the method of Example 4 was used to prepare 2.67 g of (SP-4-3)-dichloro(1-ethyl-3-pyrrolidinemethanamine-$N^1$,$N^3$)platinum, discoloration at 145°-155° C., mp 202°-206° C. (dec.)

| Analysis - For C$_7$H$_{16}$Cl$_2$N$_2$Pt | |
|---|---|
| Calc.: | C, 21.33%; H, 4.09%; N, 7.11%; Cl, 17.99% |
| Found: | C, 21.48%; H, 4.25%; N, 7.33%; Cl, 17.96%. |

Preparation of Starting Materials

Preparation of 1-Ethyl-2-aziridinemethanamine (A) Preparation of 1-Ethyl-2-cyanoaziridine A steel autoclave was charged with 20 g (94 mmol) of 2,3-dibromopropionitrile, 19 g (188 mmol) of triethylamine, 4.26 g (94 mmol) of ethylamine, and 300 ml of acetonitrile.

The autoclave and its contents were heated at 80° C. for four hours and then cooled to room temperature. The reaction mixture was filtered and the filtrate was concentrated under vacuum to produce a viscous residue. Vacuum distillation of the residue yielded 5 g (45%) of 1-ethyl-2-cyanoaziridine.

(B) Preparation of 1-Ethyl-2-aziridinemethanamine

A solution of 4.82 g (50 mmol) of 1-ethyl-2-cyanoaziridine in 10 ml of tetrahydrofuran was added dropwise to a stirred slurry of 2.37 g, 62.5 mmol of lithium aluminum hydride in 40 ml of dry tetrahydrofuran. After addition was complete, the mixture was heated to 40° C. for 17 hours. The mixture was then cooled in an ice-bath and water was cautiously added to destroy the excess reducing agent.

The reaction mixture was filtered, dried, and concentrated under vacuum to yield the product in sufficient purity to be used without further purification.

We claim:

1. A square-planar cis-platinum(II) four-coordinate complex having the formula

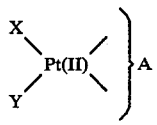

wherein A is a neutral bidentate aminoalkylcyclo(aza)alkane ligand

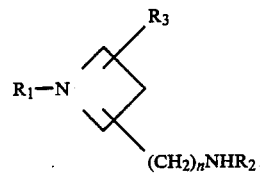

wherein n is one; $R_1$ and $R_2$ are hydrogen, and $R_3$ is methyl; wherein X and Y are negatively-charged monodentate ligands which may be the same or different and are selected from chloro, bromo, iodo, nitrato; or where X and Y taken together form a dinegatively-charged bidentate ligand selected from sulfato, oxalato,

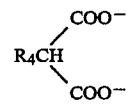

and wherein $R_4$ is hydrogen, hydroxy, amino, alkyl or from one to four carbon atoms, benzyl, hydroxyalkyl of from one to four carbon atoms, or aminoalkyl of from one to four carbon atoms; wherein the ligand A is complexed to the central platinum atom through the nitrogen atom of the cyclo(aza)alkane ring and the nitrogen atom of the aminoalkyl substituent of said group A.

2. A square-planar cis-platinum(II) four-coordinate complex as defined in claim 1 having the name (SP-4-3)-dichloro(3-methyl-3-azetidinemethaneamine-$N^1$, $N^3$)platinum.

* * * * *